United States Patent
Goel

(10) Patent No.: US 9,540,307 B2
(45) Date of Patent: Jan. 10, 2017

(54) STATINS OF OMEGA-3 POLYUNSATURATED ACIDS FOR TREATING HYPERCHOLESTEROLEMIA

(71) Applicant: Jiva Pharma, Inc., Ann Arbor, MI (US)

(72) Inventor: Om P Goel, Ann Arbor, MI (US)

(73) Assignee: JIVA PHARMA, INC., Ann Arbor, MI (US)

( * ) Notice: Subject to any disclaimer, the term of this patent is extended or adjusted under 35 U.S.C. 154(b) by 11 days.

(21) Appl. No.: 14/706,313

(22) Filed: May 7, 2015

(65) Prior Publication Data

US 2015/0322032 A1 Nov. 12, 2015

Related U.S. Application Data

(60) Provisional application No. 61/990,196, filed on May 8, 2014.

(51) Int. Cl.
| | | |
|---|---|---|
| *A01N 43/16* | (2006.01) | |
| *C07C 59/42* | (2006.01) | |
| *C07D 309/30* | (2006.01) | |
| *C07C 51/09* | (2006.01) | |

(52) U.S. Cl.
CPC ............... *C07C 59/42* (2013.01); *C07C 51/09* (2013.01); *C07D 309/30* (2013.01)

(58) Field of Classification Search
CPC .................................................... C07C 59/42
USPC ........................................................ 514/460
See application file for complete search history.

(56) References Cited

U.S. PATENT DOCUMENTS 8,188,146 B2  5/2012  Peet et al.

FOREIGN PATENT DOCUMENTS

EP  WO 2007068498  *  6/2007  .............. C12P 17/06

OTHER PUBLICATIONS

Xu HE, et al., "Molecular recognition of fatty acids by peroxisome proliferator-activated receptors", Mol. Cell. [Internet], 3(3), 397-403 (Mar. 17, 1999).
Delgado-Lista, J., et al., "Long Chain Omega-3 Fatty Acids and Cardiovascular Disease: A Systematic Review." The British J. of Nutrition, 107, Suppl. 2, S201-13 (Jun. 2012).
Holdgate G, et al. "Molecular mechanism for inhibition of 3-hydroxy-3-methylglutaryl CoA (HMG-CoA) reductase by rosuvastatin." Biochemical Society Transactions 31(3), 528-31 (2003).
Louis-Flamberg P, et al. "Slow binding inhibition of 3-hydroxy-3-methylglutaryl-coenzyme A reductase. Biochemistry." 29(17), 4115-20 (1990).
Nakamura CE, et al. "Mode of interaction of. beta.-hydroxy-. beta.-methylglutaryl coenzyme A reductase with strong binding inhibitors: compactin and related compounds." Biochemistry. 24(6), 1364-76 (1985).

* cited by examiner

*Primary Examiner* — Nizal Chandrakumar
(74) *Attorney, Agent, or Firm* — Technology Law, PLLC; Karen L. Kimble

(57) ABSTRACT

The present invention relates to novel statin derivatives of omega-3 fatty acids, and their use in treating hypercholesterolemia, obesity, hypertriglyceridemia, cardiovascular diseases, and metabolic diseases, and Alzheimer's disease.

7 Claims, 1 Drawing Sheet
(1 of 1 Drawing Sheet(s) Filed in Color)

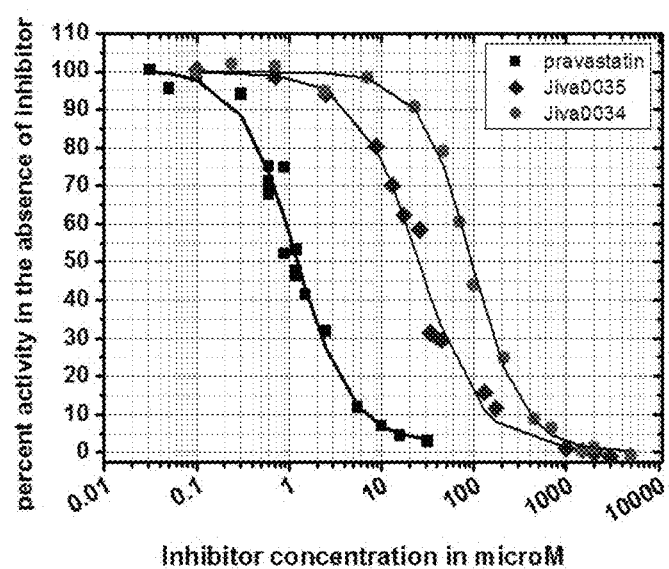

STATINS OF OMEGA-3 POLYUNSATURATED ACIDS FOR TREATING HYPERCHOLESTEROLEMIA

CROSS REFERENCE TO RELATED APPLICATIONS

This application claims priority from U.S. Provisional Application 61/990,196, filed on May 8, 2014.

FIELD OF THE INVENTION

The present invention relates to novel "omegastatins" or 'statinized' derivatives of omega-3 fatty acids used for treating hypercholesterolemia, hypertriglyceridemia, cardiovascular diseases, metabolic diseases, inflammation, or slowing down or preventing dementia of Alzheimer's disease.

BACKGROUND OF THE INVENTION

Statins, which are inhibitors of 3-hydroxy-3-methylglutaryl reductase (HMG-Coenzyme A reductase; HMG-CO-A reductase), are a class of drugs widely used to lower levels of circulating LDL (low-density lipoprotein) cholesterol, or LDL-C, known as "the bad cholesterol". The enzyme HMG-CO-A reductase plays a central role in the biosynthesis of cholesterol in the liver, which produces about 70 percent of total cholesterol in the body. Elevated LDL cholesterol level is a key risk factor for cardiovascular disease (CVD), heart attacks and strokes. Statins have been found to prevent cardiovascular disease, and heart attacks in those who are at high risk (WIKI). Besides life-style changes, such as regular exercise, eating less or avoiding fatty meals to maintain a healthy cardiovascular system, statins have become the strategic choice of treatment to achieve target LDL-C levels to prevent heart attacks, and minimize secondary or post cardiac events. Since the introduction of statins in clinical use over the last 25 years, millions of patients around the world have benefited from improved cardiovascular outcomes.

In 2013 the American College of Cardiology and American Heart Association have published widely disseminated guidelines on the use of statins (Stone N J et al., "2013 ACC/AHA Guideline on the Treatment of Blood Cholesterol to Reduce Atherosclerotic Cardiovascular Risk in Adults", *J. of the Amer. College of Cardiology* (2013), 10.1016/j.jacc.2013.11.002. Under these guidelines, more than 50 million Americans are candidates for Statin therapy (WSJ Mar. 31, 2014/B3).

The most prescribed statins are atorvastatin (Lipitor®, trademark of Pfizer); Pravastatin (Pravachol® trademark of Sankyo); rosuvastatin (Crestor® trademark of Astra-Zeneca), and simvastatin (Zocor® trademark of Merck and Co.). All these four statins, chemically, are a single diastereoisomer in the trans-3-β-hydroxy-δ-lactone portion of the molecule, which is the common key phamacophore in all the statins. The above statins are either totally synthetic (atorvastatin and rosuvastatin) or a combination of fermentation products and subsequent synthetic modifications. The effective doses range from about 10 mg to about 80 mg/day. However, in use statins are not without side-effects. Estimates are that 10-15% of people (or more than 5 million persons) suffer serious muscle pain or other side effects that prevent them from taking statins, or taking them at doses required to achieve target cholesterol levels. Rare reactions include myositis and myopathy, with the potential for rhabdomyolysis (a significant breakdown of skeletal muscle) leading to possibly acute renal failure (WIKI). Serious leg pains after prolonged use have been reported, e.g., with atorvastatin and simvastatin even at their lowest 10 mg/day dose. Thus there is a need for novel statins, which incorporate unique structural features attached to the trans-3-β-hydroxy-δ-lactone moiety of statins which have an improved safety profile than those currently used statins. It is possible that the presently conceived "omegastatins" would also concomitantly lower high triglycerides levels in addition to LDL-C.

BRIEF SUMMARY OF THE INVENTION

Omega-3 polyunsaturated acids offer an unexplored and unusual structural motif of long aliphatic carbon straight-chains rich with 4-6 conjugated, all cis double bonds of 8-12 π electrons, which is in contrast to the highly substituted heteroaromatic or bicyclic nonaromatic ring structures as found in the clinically used statins. Specifically, this invention concerns a compound of Formula (I) or Formula (II) having the formula:

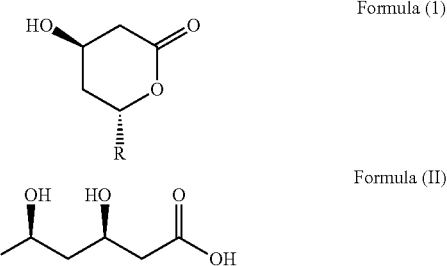

wherein:
R is joined from the aldehyde group formed by the partial reduction of the carboxylic acid of cis,cis,cis-7,10,13-hexadecatrienoic acid (HTA), cis,cis,cis-9,12,15-octadecatrienoic acid (ALA), cis,cis,cis-6,9,12,15-octadecatetraenoic acid (SDA), cis,cis,cis-11,14,17-eicosatrienoic acid (ETE), cis,cis,cis-8,11,14,17-eicosatetraenoic acid (ETA); cis,cis,cis,cis,cis-5,8,11,14,17-eicosapentanenoic acid (EPA), cis,cis,cis,cis,cis-6,9,12,15,18-heneicosapentaenoic acid (HPA), cis,cis,cis,cis,cis-7,10,13,16,19-docosapentaenoic acid (DPA), cis,cis,cis,cis,cis,cis-4,7,10,13,16,19-docosahexaenoic acid (DHA), cis,cis,cis,cis,cis-9,12,15,18,21-tetracosapentaeonic acid (TPA) or cis,cis,cis,cis,cis,cis-6,9,12,15,18,21-tetracosahexaeonic acid (THA); or
the pharmaceutically-acceptable salts of Formula (II).

These pharmaceutically-acceptable salts are preferably sodium, potassium or calcium.

Pharmaceutical formulations are made and used for the treatment of various diseases and conditions as described herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 is a graph in color where the % activity in the absence of inhibitor is plotted against the inhibitor concentration in μM where the black squares indicate pravastatin for comparison, the blue diamonds are the compound of Example 16 (ALA-lactone sodium salt), and the red circles are the compound of Example 8 (EPA-lactone sodium salt).

DETAILED DESCRIPTION OF THE INVENTION

It is understood that the terminology used herein is for the purpose of describing particular embodiments only and is not intended to be limiting. As used in this specification, the singular forms "a", "an", and "the" include plural referents unless the content clearly indicates otherwise. The following terms in the Glossary as used in this application are to be defined as stated below and for these terms, the singular includes the plural.

Various headings are present to aid the reader, but are not the exclusive location of all aspects of that referenced subject matter and are not to be construed as limiting the location of such discussion.

Also, certain US patents and PCT published applications have been incorporated by reference. However, the text of such patents is only incorporated by reference to the extent that no conflict exists between such text and other statements set forth herein. In the event of such conflict, then any such conflicting text in such incorporated by reference US patent or PCT application is specifically not so incorporated in this patent.

GLOSSARY

ALA means α-linolenic acid or cis,cis,cis-9,12,15-octadecatrienoic acid, having 18 carbons, 3 cis double bonds, that is modified by partial reduction of the carboxylic acid to its aldehyde moiety to be R of Formula (I), (8Z,11Z,14Z)-heptadeca-8,11,14-trien-5-yl)-(3R,5R)-trans-β-hydroxy-δ-lactone, and, Formula (II), ((8Z,11Z,14Z)-heptadeca-8,11,14-trien-5-yl)-(3R,5R)-3,5-dihydroxy pentanoic acid, as shown by the formula below:

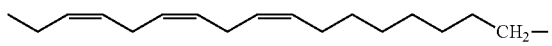

DHA means cis,cis,cis,cis,cis,cis-4,7,10,13,16,19-docosahexaenoic acid or docosahexaenoic acid, having 22 carbons, 6 cis double bonds, that is modified by partial reduction of the carboxylic acid to an aldehyde moiety to be R of Formula (I), (3Z,6Z,9Z,12Z,15Z,18Z)-henicosa-3,6,9,12,15,18-hexaen-5-yl)-(3R,5R)-trans-β-hydroxy-δ-lactone, and Formula (II), ((3Z,6Z,9Z,12Z,15Z,18Z)-henicosa-3,6,9,12,15,18-hexaen-5-yl)(3R,5R)-3,5-dihydroxy pentanoic acid, as shown by the formula below:

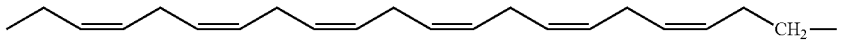

DPA means cis,cis,cis,cis,cis-7,10,13,16,19-docosapentaenoic acid or docosapentaenoic acid, having 22 carbons, 5 cis double bonds, that is modified by partial reduction of the carboxylic acid to an aldehyde moiety to be R of Formula (I), (6Z,9Z,12Z,15Z,18Z)-henicosa-6,9,12,15,18-pentaen-5-yl)-(3R,5R)-trans-β-hydroxy-δ-lactone, and Formula (II), ((6Z,9Z,12Z,15Z,18Z)-henicosa-6,9,12,15,18-pentaen-5-yl)-(3R,5R)-3,5-dihydroxy pentanoic acid, as shown by the formula below:

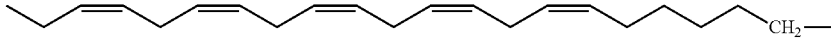

EPA means cis,cis,cis,cis,cis-5,8,11,14,17-eicosapentanenoic acid or eicosapentanenoic acid, having 20 carbons, 5 cis double bonds, that is modified by partial reduction of the carboxylic acid to an aldehyde moiety to be R of Formula (I), (4Z,7Z,10Z,13Z,16Z)-nonadeca-4,7,10,13,16-pentaen-5-yl)-(3R,5R)-trans-β-hydroxy-δ-lactone, and Formula (II), ((4Z,7Z,10Z,13Z,16Z)-nonadeca-4,7,10,13,16-pentaen-5-yl)-(3R,5R)-3,5-dihydroxy pentanoic acid, as shown by the formula below:

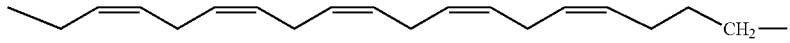

ETA means cis,cis,cis,cis-8,11,14,17-eicosatetranoic acid or eicosatetraenoic acid, having 20 carbons, 4 cis double bonds, that is modified by partial reduction of the carboxylic acid to an aldehyde moiety to be R of Formula (I), (7Z,10Z,13Z,16Z)-nonadeca-7,10,13,16-tetraen-5-yl)-(3R,5R)-trans-β-hydroxy-δ-lactone, and Formula (II), ((7Z,10Z,13Z,16Z)-nonadeca-7,10,13,16-tetraen-5-yl)-(3R,5R)-3,5-dihydroxy pentanoic acid, as shown by the formula below:

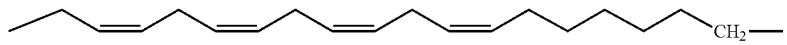

ETE means cis,cis,cis-11,14,17-eicosatrienoic acid or eicosatrienoic acid, having 20 carbons, 3 cis double bonds, that is modified by partial reduction of the carboxylic acid to an aldehyde moiety to be R of Formula (I), (10Z,13Z,16Z)-nonadeca-10,13,16-triene-5-yl)-(3R,5R)-trans-β-hydroxy-δ-lactone, and Formula (II), ((10Z,13Z,16Z)-nonadeca-10,13,16-triene-5-yl)-(3R,5R)-3,5-dihydroxy pentanoic acid, as shown by the formula below:

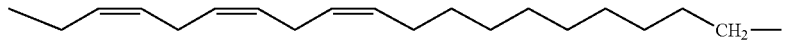

HPA means cis,cis,cis,cis,cis-6,9,12,15,18-heneicosapentaenoic acid or heneicosapentaenoic acid, having 21 carbons, 5 cis double bonds, that is modified by partial reduction of the carboxylic acid to an aldehyde moiety to be R of Formula (I), (5Z,8Z,11Z,14Z,17Z)-eicosa-5,8,11,14,17-pentaen-5-yl)-(3R,5R)-trans-β-hydroxy-δ-lactone, and Formula (II), ((5Z,8Z,11Z,14Z,17Z)-eicosa-5,8,11,14,17-pentaen-5-yl)-(3R,5R)-3,5-dihydroxy pentanoic acid, as shown by the formula below:

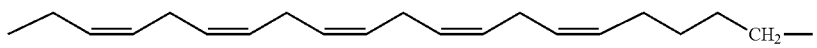

HTA means cis,cis,cis-7,10,13-hexadecatrienoic acid, having 16 carbons, 3 cis double bonds, that is modified by partial reduction of the carboxylic acid to an aldehyde moiety to be R of Formula (I), (6Z,9Z,12Z)-pentadeca-6,9,12-trien-5-yl)-(3R,5R)-trans-β-hydroxy-δ-lactone, and Formula (II), (6Z,9Z,12Z)-pentadeca-6,9,12-trien-5-yl) (3R,5R)-3,5-dihydroxy pentanoic acid, as shown by the formula below:

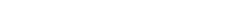

SDA means cis,cis,cis,cis-6,9,12,15-octadecatetraenoic acid or stearidonic acid, having 18 carbons, 4 cis double bonds, that is modified by the partial reduction of the carboxylic acid to an aldehyde moiety to be R of Formula (I), (5Z,8Z,11Z,14Z)-heptadeca-5,8,11,14-tetraen-5-yl) (3R,5R)-trans-β-hydroxy-δ-lactone, and Formula (II), (5Z,8Z,11Z,14Z)-heptadeca-5,8,11,14-tetraen-5-yl) (3R,5R)-3,5-dihydroxy pentanoic acid, as shown by the formula below:

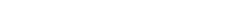
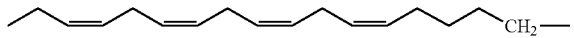

THA means cis,cis,cis,cis,cis,cis-6,9,12,15,18,21-tetracosahexaenoic acid, having 24 carbons, 6 cis double bonds, that is modified by reduction of the carboxylic acid to an aldehyde moiety to be R of Formula (I), (5Z,8Z,11Z,14Z,17Z,20Z)-tricosa-5,8,11,14,17,20-hexaen-5-yl)-(3R,5R)-trans-β-hydroxy-δ-lactone, and Formula (II), ((5Z,8Z,11Z,14Z,17Z,20Z)-tricosa-5,8,11,14,17,20-hexaen-5-yl)-(3R,5R)-3,5-dihydroxy pentanoic acid, as shown by the formula below:

TPA means cis,cis,cis,cis,cis-9,12,15,18,21-tetracosapentaeonic acid, having 24 carbons, 5 cis double bonds, that is modified by partial reduction of the carboxylic acid to an aldehyde moiety to be R of Formula (I), (8Z,11Z,14Z,17Z,20Z)-tricosa-8,11,14,17,20-pentaen-5-yl)-(3R,5R)-trans-β-hydroxy-δ-lactone, and Formula (II), ((8Z,11Z,14Z,17Z,20Z)-tricosa-8,11,14,17,20-pentaen-5-yl) (3R,5R)-3,5-dihydroxy pentanoic acid as shown by the formula below:

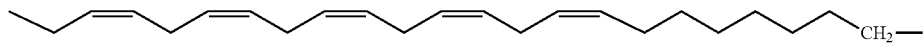

Omega-3 fatty acids means naturally occurring, straight-chain $C_{16}$-$C_{24}$, all cis; conjugated, polyunsaturated fatty carboxylic acids PUFA means polyunsaturated fatty acids that are either naturally occurring omega-3 fatty acids or derivatives thereof DIBALH means diisobutylaluminumhydride HMG-CO-A reductase or HMG-Coenzyme A reductase means 3-hydroxy-3-methylglutaryl reductase LDA means lithium diisopropylamide RT means room temperature or ambient temperature or about 22 to about 25° C.

rt means retention time in the context of reporting high performance chromatographic purity data THF means tetrahydrofuran % means percent by weight unless stated otherwise General Discussion Poly-unsaturated fatty acids (PUFAs), such as the omega-3 acids, have been shown to interact with, and in some cases activate the transcriptional activity of, PPARγ receptor (Xu H E, et al., "Molecular recognition of fatty acids by peroxisome proliferator-activated receptors", *Mol. Cell.* [Internet], 1999 Mar. 17, 3(3), 397-403. Among the omega-3 fatty acids eicosapentanenoic acid (EPA, 20 carbons, 5 conjugated carbon-carbon double bonds), docohexaenoic acid (DHA, 22 carbons, 6 conjugated double bonds) are the most studied pharmacologically. Pharmaceutically effective mixtures of ethyl esters of eicosapentaenoic acid and docosahexaneoic acid are prescribed to treat hypertriglyceridemia. Triglycerides form in the liver, and since ~70% of body's cholesterol is biosynthesized in the liver with the essential involvement of the key enzyme HMG-CO-A-reductase, this invention transforms the carboxylic group of the PUFAs into a trans-3-β-hydroxy-δ-lactone moiety and provides novel statins with improved safety profiles for cardiovascular health, preventing strokes, and reducing blood pressure. These omega-3 acids in their natural tri- and bis-glyceride forms are consumed in 1-4 g/day as dietary supplements so their safety is known. (Delgado-Lista, J., et al., "Long Chain Omega-3 Fatty Acids and Cardiovascular Disease: A Systematic Review." *The British J. of Nutrition* 107 Suppl. 2: S201-13 (June 2012)).

Omega-3 oils or omega-3 fatty acids are naturally occurring, straight-chain (16-24 carbons) polyunsaturated fatty carboxylic acids (PUFAs), essential for normal metabolism in humans and other animals. PUFAs have 3-6 conjugated carbon-carbon double bonds, and are so named as the first carbon with unsaturation is $3^{rd}$ carbon from the distal carboxylic acid carbon. All double bonds are in the cis configuration. Among the omega-3 fatty acids eicosapentanenoic acid (EPA, 20 carbons, 5 conjugated carbon-carbon double bonds), docohexaenoic acid (DHA, 22 carbons, 6 conjugated double bonds) and α-linolenic acid (ALA, 18 carbons, 3 conjugated double bonds) are the most studied pharmacologically. Surprisingly, the compounds of this invention having both PUFA-like moieties and a terminal trans-β-hydroxy-δ-lactone functionality have not been synthesized or reported upon.

These statin derivatives of PUFAs of the present invention are formed by the partial reduction of the carboxylic acid of the omega-3s to an aldehyde functionality, which carbon than becomes incorporated in the trans-β-hydroxy-δ-lactone functionality as indicated by an asterisk (*) in Formula (I) and Formula (II) below. R denotes the rest of the PUFA structure, the end methylene moiety of the PUFA becomes a bridge linked to the trans-β-hydroxy-δ-lactone ring.

The absolute configuration present at the two chiral centers in the trans-β-hydroxy-δ-lactone moiety are: 3-(R), 5-(R). The following structure depicts these present compounds of Formula (I). The compounds of Formula (II) are the syn-β,δ-dihydroxy carboxylic acids obtained by hydrolysis of compounds of Formula (I) as shown in Scheme 1:

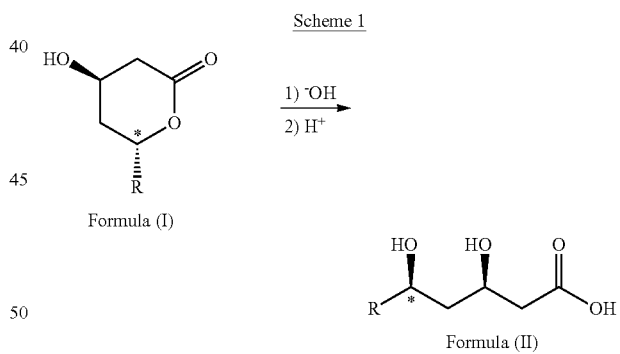

wherein: R is joined to the carbon formed by partial reduction to an aldehyde functionality of the carboxylic acid of cis,cis,cis-7,10,13-hexadecatrienoic acid (HTA), cis,cis,cis-9,12,15-octadecatrienoic acid (ALA), cis,cis,cis,cis-6,9,12,15-octadecatetraenoic acid (SDA), cis,cis,cis-11,14,17-eicosatrienoic acid (ETE), cis,cis,cis,cis-8,11,14,17-eicosatetraenoic acid (ETA); cis,cis,cis,cis,cis-5,8,11,14,17-eicosapentanenoic acid (EPA), cis,cis,cis,cis,cis-6,9,12,15,18-heneicosapentaenoic acid (HPA), cis,cis,cis,cis,cis-7,10,13,16,19-docosapentaenoic acid (DPA), cis,cis,cis,cis,cis,cis-4,7,10,13,16,19-docosahexaenoic acid (DHA), cis,cis,cis,cis,cis-9,12,15,18,21-tetracosapentaeonic acid (TPA) or cis,cis,cis,cis,cis,cis-6,9,12,15,18,21-tetracosahexaeonic acid (THA).

Both compounds of Formula (I) and Formula (II) are physiologically active for a variety of uses as further described below.

The present invention provides both trans-β-hydroxy-δ-lactones of Formula (I) and (3R,5R)-3,5-dihydroxy pentanoic acids of Formula (II) derived from the above polyunsaturated omega-3 fatty acids (PUFAs) as their "statins" to treat hypercholesterolemia, and as depicted by the following Formulas (I) and (II):

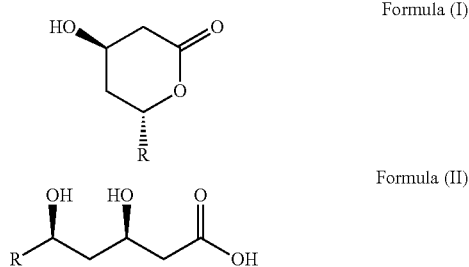

R is joined from the aldehyde group formed by the partial reduction of the carboxylic acid of cis,cis,cis-7,10,13-hexadecatrienoic acid (HTA), cis,cis,cis-9,12,15-octadecatrienoic acid (ALA), cis,cis,cis-6,9,12,15-octadecatetraenoic acid (SDA), cis,cis,cis-11,14,17-eicosatrienoic acid (ETE), cis,cis,cis-8,11,14,17-eicosatetraenoic acid (ETA); cis,cis,cis,cis-5,8,11,14,17-eicosapentanenoic acid (EPA), cis,cis,cis,cis-6,9,12,15,18-heneicosapentaenoic acid (HPA), cis,cis,cis,cis-7,10,13,16,19-docosapentaenoic acid (DPA), cis,cis,cis,cis,cis-4,7,10,13,16,19-docosahexaenoic acid (DHA), cis,cis,cis,cis,cis-9,12,15,18,21-tetracosapentaeonic acid (TPA) or cis,cis,cis,cis,cis-6,9,12,15,18,21-tetracosahexaeonic acid (THA).

Compounds of Formula (I) can be used alone as a pharmaceutically-acceptable formulation, or compounds of Formula (II) and their pharmaceutically acceptable salts in formulations, such as a tablet, capsule, emulsions, suspensions, or other formulations to treat hypercholesterolemia. The pharmaceutically acceptable salts of compounds of Formula (II) are sodium, potassium and calcium and have water solubility such that injectable solutions and ampoules are also possible formulations.

Alzheimer' Disease (AD):

The prevalence and incidence of Alzheimer's disease, and its devastating effects on the lives of patients and care giver families are well known. The health care costs to society are onerous, and will continue to grow with the aging population. Enormous strides have been made in understanding the pathology of the disease which leads to the build-up of amyloid plaques in the brain, which are aggregates of amyloid beta (Aβ) peptides. Fundamental advances have been made in discovering inhibitors of the extra-cellular and intra-cellular neuronal biochemical enzymes such as β-secretage (BACE1) or γ-secretase (GS) to stop the amyloid or intraneuronal τ-tangles build-up; and even reverse these processes through treatment with specific monoclonal antibodies. However, in spite of massive scientific research and investments in reversing the cognitive decline of AD, these efforts have yielded scant benefits. Consensus is emerging that the best approach would be to treat before the disease has progressed too far, and even before disease symptoms become apparent. Multi-targeted Alzheimer's drugs, for example dual BACE/acetylcholinesterase inhibition or GSM/PPARγ active agents would offer additional benefits (Harrie J. M. Gisjen, et al., "Secretase Inhibitors and Modulators as a Disease-Modifying Approach Against Alzheimer's Disease"; *Annual Reports in Medicinal Chem.*, 47, 55-69 (2012)).

High doses of statins prevent dementia in older people, according to research presented in 2014, at the ESC Congress by Dr. Tin-Tse Lin from Taiwan. The study of nearly 58,000 patients found that high potency statins had the strongest protective effects against dementia. In a further study by Dr. Lin of nearly 1 million patients over 4.5 years concluded "The adjusted risks for dementia were significantly inversely associated with increased total or daily equivalent statin dosage. Patients who received the highest total equivalent doses of statins had a 3-fold decrease in the risk of developing dementia. Similar results were found with the daily equivalent statin dosage." The study found that "high doses of statins, particularly high potency statins, prevent dementia."

The presence of omega-3 fatty acids, especially DHA in the brain is ubiquitous. Clinical studies in 4 year old children support the beneficial effects of docohexaenoic acid (DHA) on cognitive function (NCT 00351624; 2006-2008; sponsored by Martek BioSciences Corporation). Therefore, it would be worth exploring in a prospective study, if a DHA-statin of the present invention, either alone, or in combination with a gamma secretase modulator (GSM), or other prescribed clinical agents would slow down the decline of cognitive function in pre- or early stage AD patients.

This invention will be further clarified by a consideration of the following general examples of synthesis of compounds of Formula (I) and Formula (II) which are intended to be purely exemplary of the present invention. The various compounds have been named and an abbreviation added in parenthesis that is used in these examples.

General Preparation of:
1) (4R,6R)-4-Hydroxy-6-((4Z,7Z,10Z,13Z,16Z)-nonadeca-4,7,10,13,16-pentaenyl)tetrahydro-2H-pyran-2-one, (EPA-lactone)

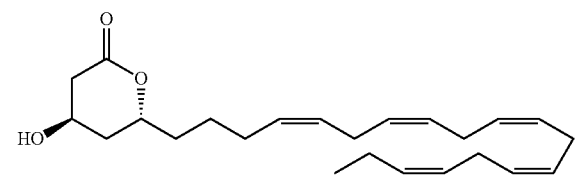 [SMILES: CC/C=C\C/C=C\C/C=C\C/C=C\C/C=C\CCC[C@@H]1C[C@@H](O)CC(=O)O1]

2) Sodium (3R,5R,9Z,12Z,15Z,18Z,21Z)-3,5-dihydroxytetracosa-9,12,15,18,21-pentaenoate, (EPA-lactone-sodium salt)

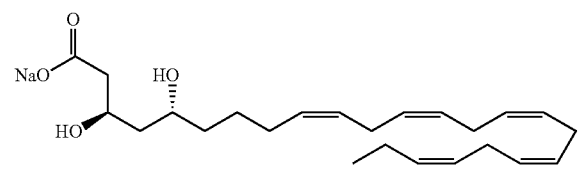

3) (4R,6R)-6-((8Z,11Z,14Z)-Heptadeca-8,11,14-trienyl)-4-hydroxytetrahydro-2H-pyran-2-one, (ALA-lactone)

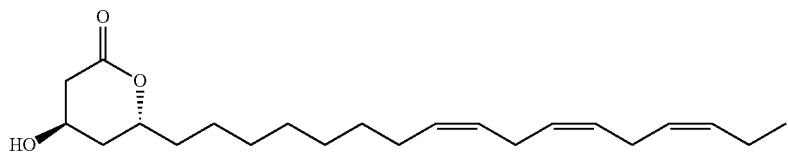 [SMILES: CC/C=C\C/C=C\C/C=C\CCCCCCC[C@@H]1C[C@@H](O)CC(=O)O1]

4) Sodium (3R,5R,13Z,16Z,19Z)-3,5-dihydroxydocosa-13,16,19-trienoate, (ALA-lactone-sodium salt)

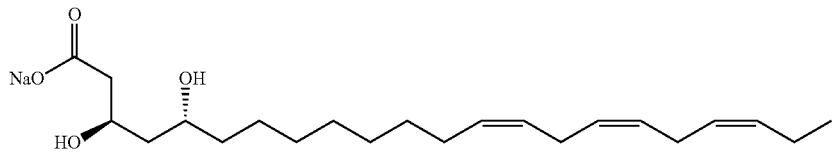

General Process Discussion:

The eicosapentaenoic (EPA) lactone, alpha linolenic acid (ALA) lactone, and the corresponding sodium salts were prepared in 8-9 steps from EPA ester and ALA acid in analogy to the literature procedures for atorvastatin analogs [Roth, B. D. et al., *J. Med. Chem.* 33, 21 (1990); Sliskovic, D. R. et al., *J. Med. Chem.* 33, 33 (1990)].

Scheme 2

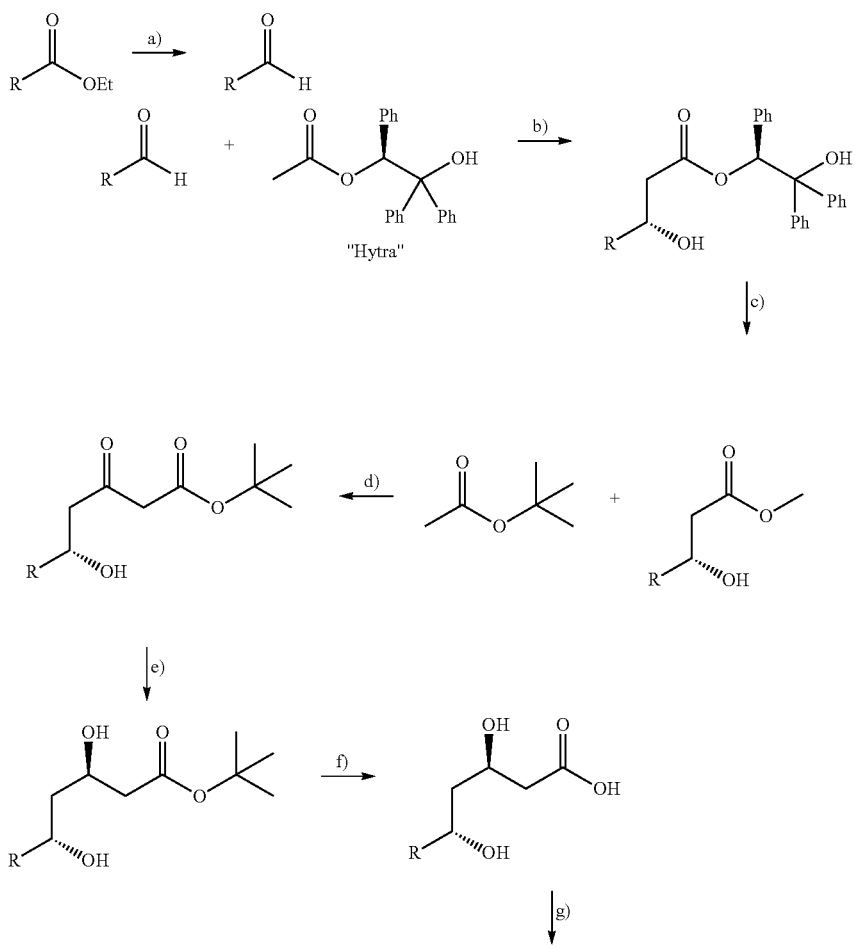

-continued

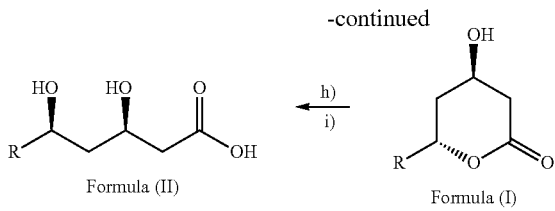

Formula (II) ← h) i) ← Formula (I)

In the above Scheme 2, Ph means phenyl, Me means methyl, Et means ethyl, and the various steps are performed using the following conditions:

a) DIBALH, THF, −78° C.; b) LDA, THF, −78° C.; c) NaOMe, MeOH, RT; d) LDA, THF, −78° C.; e) NaBH$_4$, Et$_3$B; f) NaOH, H$_2$O-MeOH/THF; g) heat (about 25-50° C.); h) NaOH, H$_2$O-MeOH/THF; i) 5% aqueous HCl.

Synthesis Overview:

The ethyl ester of EPA was converted to the aldehyde using a slight excess DIBAH at −78° C. The reaction produced a mixture of mostly EPA aldehyde (60-80%) and the corresponding alcohol (20-40% yield) by-product, which was separated by column chromatography. For alpha linolenic acid, the aldehyde was prepared by reduction of the ALA acid with LAH, followed by oxidation to the aldehyde with Des s-Martin periodinane in yields of 60-80% for 2 steps. The aldehydes were then coupled with the chiral auxiliary, Hytra, at −78° C. The experiment produced a mixture that was predominantly the desired isomer (85:15). The yield was reduced both because a significant amount of aldol condensation products (from the aldehyde condensing with itself) were present, and the product was contaminated with Hytra, which was difficult to separate by column chromatography. The methyl ester was displaced with an excess of the lithium salt of t-butyl acetate at −50° C. to form the keto ester in reasonable yield (70-90%). The keto ester was treated with methoxydiethylborane to form the borate complex that was reduced with sodium borohydride at −78° C. The reduction produced primarily the desired isomer (3:1) of the hydroxy ester. However, the yield was reduced significantly, because the borate complex is destroyed with hydrogen peroxide which causes some oxidative side products. The purification by column chromatography was also difficult and only a portion of the undesired isomer could be removed. The t-butyl group was removed with trifluoroacetic acid to form the lactone in somewhat low yield due to the carry-over of side-products from previous steps and some decomposition during the deprotection step.

For the EPA lactone, the EPA ester (~25 g) was converted in seven steps to the EPA lactone in two or three batches for each step, to yield 1.0 g of the pure lactone, after two purifications to remove the unwanted isomer.

For the ALA lactone, ALA acid (10 g) was converted to the lactone (0.64 g) over 8 steps. A portion of each lactone (~100 mg) was converted to the corresponding sodium salt.

This invention will be further clarified by consideration of the following specific examples of syntheses of compounds of Formula (I) and Formula (II) which are intended to be purely exemplary of the present invention.

The following reactions were derived from prior processes by:

Lentsch, C.; Rinner, U.; "General synthesis of highly functionalized cyclopentane segments for the preparation of jatrophane diterpenes." Org. Lett., 11(22), 5326-5328, 2009.

Brian, C. T.; et al.; "Synthesis of macrocyclic precursors of lankacidins using Stille reactions of 4-(2-iodoalkenyl) azetidinones and related compounds for ring closure." Tetrahedron, 66(33), 6613-6625, 2010.

Rudolph, M.; et al.; "High chemo selectivity in the phenol synthesis." Beil. J. of Org. Chem., 7, No. 90, 794-801, 2011.

Smith, T. E.; et al.; "Stereochemically versatile synthesis of the C1-C12 fragments of tedanolide C." Org. Lett., 14(6), 1452-1455, 2012.

Miller, A.; et al.; "An efficient large scale preparation of (S)-1, 1,2-triphenylethanediol 2-acetate." Org. Prep. & Proc. Int., 23(2), 173-180, 1991.

Example 1

EPA-Aldehyde

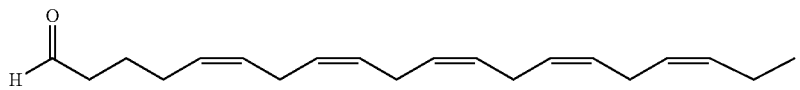

EPA ethyl ester (97%, Nutegrity, 20.0 g, 0.065 mol) was dissolved in dichloromethane (120 mL) under an argon atmosphere. The solution was cooled in acetone-dry ice batch and 1M diisobutylaluminum hydride (115 mL) in dichloromethane was added drop-wise over 1 hour. After addition, the solution stirred for 3 hours at −78° C. The reaction mixture was quenched with saturated ammonium chloride (100 mL) added drop-wise followed by 5% HCl (100 mL). Additional dichloromethane (200 mL) was added and the mixture warmed to RT. After filtration, the dichloromethane layer was separated, dried over anhydrous sodium sulfate, filtered, and concentrated. The crude EPA aldehyde (19.2 g, yellow oil) was purified by column chromatography on silica gel (250 g) eluting with ethyl acetate/heptanes (1:20) to give EPA aldehyde as a clear oil (12.9 g, 79% yield, pure by NMR) and is characterized by the following spectra:

$^1$H NMR (300 MHz, CDCl$_3$/TMS): δ 9.78 (s, 1H), 5.50-5.22 (m, 12H), 2.90-2.75 (m, 10H), 2.51-2.45 (m, 4H), 2.08 (m, 2H), 0.98 (t, 3H J=7.5 Hz).

$^{13}$C NMR (75 MHz, CDCl$_3$/TMS): δ 201.7, 132.2, 128.6, 128.7, 128.6, 128.5, 128.1, 127.9, 127.2, 44.0, 26.0, 25.9, 20.9, 20.5, 14.6.

Example 2

Hytra

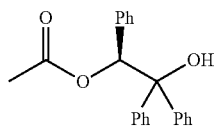 [SMILES: CC(=O)O[C@@H](c1ccccc1)C(O)(c1ccccc1)c1ccccc1]

(S)-1,1,2-Triphenylethane-1,2-diol (Alfa Aesar, 9.5 g, 32.7 mmol) was dissolved in dichloromethane (200 mL) under an argon atmosphere. The flask was cooled in an ice-water bath, and acetyl chloride (6.0 g, 76.4 mmol) was added. Pyridine (8.0 g, 82 mmol) was added drop-wise over 5 minutes. After 2 hours, the product was filtered. The product was dissolved in dichloromethane (2 L) and extracted with 5% aqueous hydrochloric acid (150 mL) and water (150 mL). The dichloromethane solution was dried over anhydrous sodium sulfate, filtered, concentrated (to 40 mL) and stored in a freezer for two hours. The solid product was collected on a funnel, washed with dichloromethane (15 mL) and dried under high vacuum overnight. The experiment produced Hytra as a white solid (10.1 g, 93% yield) and is characterized by the following spectra:

$^1$H NMR (300 MHz, DMSO-$d_6$): δ 7.48 (d, 2H, J=7.5 Hz), 7.33-7.23 (m, 5H), 7.18-7.05 (m, 8H), 6.58 (s, 1H), 6.14 (s, 1H), 1.93 (s, 3H).

Example 3

EPA-Hytra Condensation

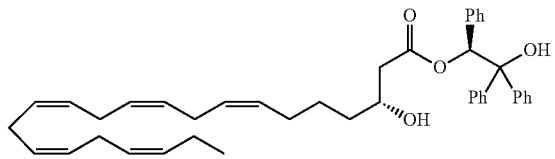

Hytra (prepared as in Example 2, 5.50 g, 16.5 mmol) was added to dry THF (100 mL) under an argon atmosphere. The slurry was cooled in a dry ice/acetone bath. LDA solution (2.5 M, 20 mL, 50 mmol) was added drop-wise over 10 minutes. The mixture was slowly warmed to −10° C. over 2 hours, and stirred further for 30-40 minutes at −10° C. The solution was cooled again to −78° C. and the EPA-aldehyde (6.56 g, 22.9 mmol) in THF (20 mL) was added drop-wise over 30 minutes. The mixture was stirred for 2 hours at −78° C. under argon. The reaction was quenched at −78° C. with a drop-wise addition of saturated ammonium chloride solution (100 mL). The solution was warmed to −5° C. and diluted with water (100 mL). The mixture was extracted twice with ethyl acetate (150 mL). The ethyl acetate extracts were combined, dried over anhydrous magnesium sulfate, filtered, and concentrated on a rotary evaporator. The crude oil (12.4 g) was purified by column chromatography on silica gel (200 g), eluting with 5-100% ethyl acetate in heptane. The experiment produced the aldol product (8.4 g, 82% yield) which was contaminated with Hytra (15-20%) and is characterized by the following spectra:

$^1$H NMR (300 MHz, CDCl$_3$/TMS): δ 7.56 (d, 2H, J=7.8 Hz), 7.33-7.23 (m, 5H), 7.18-7.00 (m, 8H), 6.72 (s, 1H), 5.40-5.25 (m, 10H), 3.80 (m, 1H), 2.84-2.70 (m, 8H), 2.40-2.30 (m, 2H), 2.10-2.00 (m, 4H), 1.50-1.25 (m, 4H), 0.97 (t, 3H, J=7.5 Hz).

Example 4

EPA-Hydroxy Methyl Ester

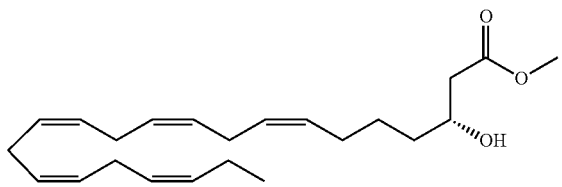 [SMILES: CC/C=C\C/C=C\C/C=C\C/C=C\C/C=C\CCC[C@@H](O)CC(=O)OC]

The EPA-Hytra condensation product (prepared as in Example 3, 8.3 g, 13.4 mmol), was dissolved in anhydrous methanol (200 mL) under an argon atmosphere. The flask was cooled in a water/ice bath and 0.5 M sodium methoxide solution in methanol (20 mL) was added. The solution stirred for 2 hours while cooling in a water/ice bath under argon. After 2 hours, 5% hydrochloric acid solution (50 mL) was added and the methanol was removed on a rotary evaporator. The mixture was diluted with water (100 mL), and the product extracted with dichloromethane (100 mL). The aqueous extract was extracted a second time with dichloromethane (50 mL). The dichloromethane extracts were combined, dried over anhydrous magnesium sulfate, filtered and concentrated. The residue oil was mixed with heptane (50 mL) and stored in a freezer overnight. The solid ((S)-1,1,2-triphenylethane-1,2-diol) was removed by filtration, washing with cold heptane (10 mL). The heptane filtrate was concentrated and purified over silica gel (240 g) eluting with 10% ethyl acetate in heptane. The experiment produced the EPA-hydroxy methyl ester as a clear oil (4.1 g, 85% yield) that still contained 5-10% of (S)-1,1,2-triphenylethane-1,2-diol and is characterized by the following spectra:

$^1$H NMR (300 MHz, CDCl$_3$/TMS): δ 5.40-5.25 (m, 10H), 4.01 (m, 1H), 3.72 (s, 3H), 2.84-2.70 (m, 8H), 2.60-2.30 (m, 2H), 2.10-2.00 (m, 4H), 1.57-1.40 (m, 4H), 0.98 (t, 3H, J=7.5 Hz).

Example 5

EPA-Keto Ester

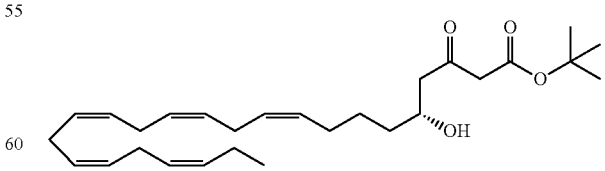

t-Butyl acetate (5.80 g, 50 mmol) was dissolved in THF (50 mL) under an argon atmosphere. The flask was cooled in an acetone/dry ice bath. Lithium diisopropylamide solution (2.5 M, 16 mL, 40 mmol) was added drop-wise over 5 minutes. The solution was allowed to stir for 30 minutes at −78° C. The EPA-hydroxy methyl ester (3.60 g, 10 mmol) in THF (20 mL) was added drop-wise over 5-10 minutes at −78° C. under argon. The solution slowly warmed to −50° C., over 1 hour. The temperature was maintained at −50° C. for 2 hours and then was slowly raised to −15° C. over 2 hours. The mixture stirred more at −15° C. for 20 minutes, and then quenched with the addition of saturated aqueous ammonium chloride solution (5 mL). The reaction mixture was diluted with 5% hydrochloric acid solution (100 mL), and extracted with ethyl acetate (2×50 mL). The ethyl acetate extracts were combined, dried over anhydrous sodium sulfate, filtered, and concentrated. The crude product (4.11 g) was purified by column chromatography on silica gel (200 g) eluting with 10% ethyl acetate in heptane. The experiment produced the EPA-keto ester (4.1 g, 92% yield) as a clear oil. The product contained some of the ester starting material (10%) along with the ((S)-1,1,2-triphenylethane-1,2-diol (5-10%) from the previous step and is characterized by the following spectra:

$^1$H NMR (300 MHz, CDCl$_3$/TMS): δ 5.40-5.25 (m, 10H), 4.06 (m, 1H), 3.37 (s, 2H), 2.84-2.75 (m, 8H), 2.75-2.50 (m, 2H), 2.10-2.00 (m, 4H), 1.57-1.40 (m, 4H), 1.49 (s, 9H), 0.97 (t, 3H, J=7.5 Hz).

Example 6

EPA-Dihydroxy t-Butyl Ester

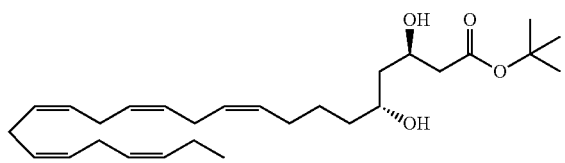 [SMILES: CC/C=C\C/C=C\C/C=C\C/C=C\C/C=C\CCC[C@@H](O)CC(=O)CC(=O)OC(C)(C)C]

The keto-ester (4.1 g, 9.22 mmol) was dissolved in THF (80 mL) and methanol (20 mL) under argon. The solution was cooled to 5° C., and 1M diethylmethoxy borane solution (12 mL) was added drop-wise over 5 minutes. After 20 minutes, the solution was cooled to −78° C. in a dry ice/acetone bath. Sodium borohydride (900 mg, 23.8 mmol) was added and the mixture stirred for 3 hours at −78° C. The mixture was slowly warmed to −25° C. over 45 minutes. At −25° C., THF (60 mL) and water (20 mL) containing sodium acetate (2.0 g) was added. Hydrogen peroxide solution (30%, 20 mL) was added drop-wise over 5-10 minutes and the reaction mixture allowed to warm to RT over 2 hours. The solution stirred for an additional 30 minutes at RT. The solution was cooled again in an ice/water bath, and saturated sodium sulfite solution (100 mL) was added drop-wise over 30 minutes. The product was then extracted with ethyl acetate (2×100 mL). The combined ethyl acetate extracts were washed with water (2×50 mL), dried over sodium sulfate, filtered, and concentrated. The crude oil (4.9 g) was purified by column chromatography on silica gel (175 g), eluting with 15% ethyl acetate in heptane. The experiment produced the EPA-dihydroxy t-butyl ester (3.08 g, 75% yield) as a clear oil, which still contained a small amount of the undesired isomer (10-20%) and is characterized by the following spectra:

$^1$H NMR (300 MHz, CDCl$_3$/TMS): δ 5.40-5.25 (m, 10H), 4.22 (m, 1H), 3.87 (m, 1H), 2.84-2.75 (m, 8H), 2.39 (d, 2H, J=6.0 Hz), 2.10-2.00 (m, 4H), 1.60-1.40 (m, 4H), 1.46 (s, 9H), 0.97 (t, 3H, J=7.5 Hz).

Example 7

EPA-Lactone

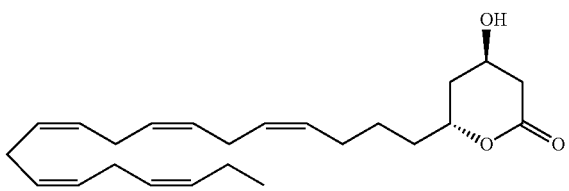 [SMILES: CC/C=C\C/C=C\C/C=C\C/C=C\C/C=C\CCC[C@@H]1C[C@@H](O)CC(=O)O1]

The EPA-dihydroxy t-butyl ester 6, (2.4 g, 5.4 mmol) was dissolved in dichloromethane (75 mL), under an argon atmosphere. Trifluoroacetic acid (1.1 mL) was added and the solution stirred for 24 hours under argon at RT. The solution was concentrated and the crude lactone was purified by column chromatography on silica gel (100 g), eluting with 40% ethyl acetate in heptane. The experiment generated the EPA-lactone (1.28 g, 64% yield) as a light yellow oil that still contained a trace amount of the undesired isomer (5-10% by NMR).

The seven step reaction was repeated on the same scale to produce additional EPA-lactone (1.2 g). The batches were combined and purified a second time by column chromatography on silica gel (80 g) eluting with 40% ethyl acetate in heptane. The second purification provided pure EPA-lactone (1.06 g) as a light yellow oil and is characterized by the following characteristics and spectra:

| Name: | (4R,6R)-4-hydroxy-6-((4Z,7Z,10Z,13Z,16Z)-nonadeca-4,7,10,13,16-pentaenyl)tetrahydro-2H-pyran-2-one |
|---|---|
| Appearance: | light yellow oil |
| Chemical Formula: | $C_{24}H_{36}O_3$ |
| Molecular Weight: | 372.54 |
| Chromatographic purity (HPLC): | 99.6% (rt = 12.597 min, 90-100% MeOH in H$_2$O over 15 minutes, Altima C18, 5μ, 4.6 × 250 mm, 1.0 mL/min, 10 μL injection, 40° C., UV detection, 210 nm). |
| Optical Rotation: | $[\alpha]_D^{22}$ = +8.767 (c = 1.56, ethanol) |
| HRMS (MMI-TOF-MS): | Calculated for $C_{25}H_{36}O_3$ (M + H)$^+$: 373.2737; found: 373.2745. |
| $^1$H NMR (300 MHz, CDCl$_3$/TMS): | δ 5.40-5.25 (m, 10 H), 4.70 (m, 1H), 4.36 (m, 1H), 2.88-2.74 (m, 8H), 2.72-2.50 (m, 2H), 2.15-1.90 (m, 4H), 1.78-1.40 (m, 6H), 0.98 (t, 3H, J = 7.8 Hz). |

Example 8

EPA-Lactone, Sodium Salt

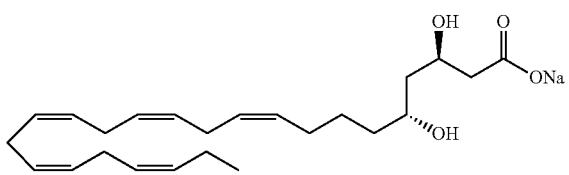

The EPA-lactone (100 mg, 0.29 mmol) was dissolved in THF (2 mL) and methanol (2 mL) under an argon atmosphere. To the solution was added sodium hydroxide (12 mg, 0.30 mmol) in water (2 mL). The solution stirred for 18 hours at RT under argon. The solution was concentrated and dried under high vacuum. The experiment produced the sodium salt of EPA-lactone as a light yellow gel (112 mg, 100% yield, and 90% purity by NMR) and is characterized by the following spectra:

$^1$H NMR (300 MHz, CD$_3$OD): δ 5.40-5.25 (m, 10H), 4.09 (m, 1H), 3.76 (m, 1H), 2.88-2.76 (m, 8H), 2.40-2.22 (m, 4H), 2.15-2.00 (m, 4H), 1.65-1.40 (m, 4H), 0.97 (t, 3H, J=7.5 Hz).

Example 9

ALA-Alcohol

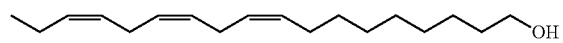

Lithium aluminum hydride powder (3.33 g, 0.877 mol) was transferred to a 500 mL flask under argon atmosphere. Anhydrous THF (120 mL) was added and the flask cooled in an ice/water bath. Alpha-linolenic acid (10.0 g, 0.036 mol) in THF (40 mL) was added drop-wise over 15 minutes, and the mixture stirred for three hours at 5° C. under argon. After 3 hours, the reaction was quenched by drop-wise addition of saturated sodium sulfate (15 mL) over 30 minutes. Anhydrous sodium sulfate (25 g) was added and the mixture stirred for 30 minutes at RT. The solids were removed by filtration, washing with THF (20 mL). The THF filtrate was further dried over anhydrous sodium sulfate, filtered, and concentrated. The crude ALA-alcohol (9.1 g, 96% yield) was used in the next step without purification and is characterized by the following spectra for the crude product:

$^1$H NMR (300 MHz, CDCl$_3$/TMS): δ 5.40-5.25 (m, 6H), 3.641 (t, 2H, J=6.6 Hz), 2.81 (m, 4H), 2.11-2.04 (m, 4H), 1.60-1.50 (m, 2H), 1.50-1.20 (m, 12H), 0.97 (t, 3H, J=7.5 Hz).

Example 10

ALA-Aldehyde

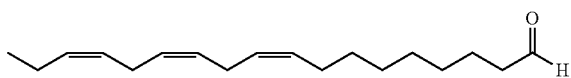 [SMILES: CC/C=C\C/C=C\C/C=C\CCCCCCCC=O]

The ALA-alcohol (prepared as in Example 9, 9.1 g, 34.5 mmol) was dissolved in dichloromethane (250 mL) under an argon atmosphere. The flask was cooled in an ice/water bath, and Dess-Martin periodinane (30 g, 70.7 mmol) was added in portions over 2-3 hours. The reaction mixture was slowly allowed to warm to RT over 2 hours. The mixture was filtered through a pad of Celite® (Sigma-Aldrich) and washed with water (200 mL). The dichloromethane solution was dried over anhydrous sodium sulfate, filtered, and concentrated. The residual oil was purified by column chromatography on silica gel (200 g) eluting with 1:4 ethyl acetate in heptane. The experiment generated the ALA-aldehyde as a light yellow oil (8.2 g, 91% yield) and is characterized by the following spectra:

$^1$H NMR (300 MHz, CDCl$_3$/TMS): δ 9.77 (s, 1H), 5.40-5.25 (m, 6H), 2.81 (m, 4H), 2.43 (dt, 2H, J=7.5, 1.8 Hz), 2.11-2.04 (m, 4H), 1.70-1.50 (m, 2H), 1.40-1.25 (m, 10H), 0.98 (t, 3H, J=7.5 Hz).

Example 11

ALA-Hytra Condensation

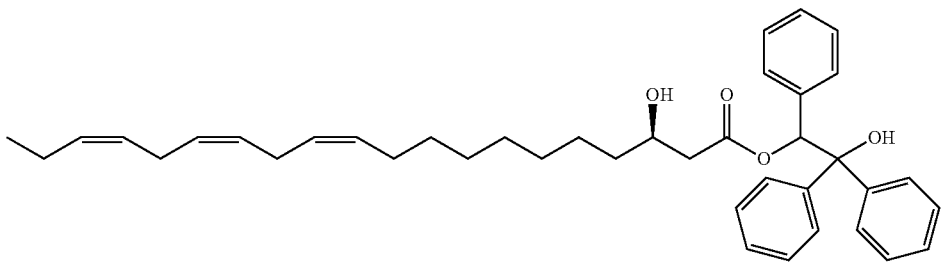 [SMILES: CC/C=C\C/C=C\C/C=C\CCCCCCC[C@@H](O)CC(=O)OC(c1ccccc1)C(O)(c1ccccc1)c1ccccc1]

Hytra (prepared as in Example 2, 8.3 g, 25 mmol) was added to dry THF (120 mL) under an argon atmosphere. The slurry was cooled with a dry ice/acetone bath to −78° C. LDA solution (2.0 M, 33 mL, 66 mmol) was added drop-wise over 15 minutes. The mixture was slowly warmed to −10° C. over 2 hours, and stirred for 30-40 minutes at −10° C. The solution was cooled again to −78° C. and the ALA-aldehyde (8.1 g, 30.9 mmol) in THF (20 mL) was added drop-wise over 30 minutes. The mixture was stirred for 2 hours at −78° C. under argon. The reaction mixture was quenched at −78° C. with a drop-wise addition of saturated ammonium chloride solution (100 mL). The solution was warmed to −5° C. and diluted with water (100 mL). The mixture was extracted twice with ethyl acetate (150 mL). The ethyl acetate extracts were combined, dried over magnesium sulfate, filtered, and concentrated on a rotary evaporator. The crude oil was stirred in dichloromethane (250 mL) and stored at −10° C. overnight. The unreacted Hytra was removed by filtration. The filtrate was concentrated and purified by column chromatography on silica gel (200 g), eluting with 5-100% ethyl acetate in heptane. The experiment produced the aldol product (5.52 g, 37% yield) which was contaminated with Hytra (20%) and is characterized by the following spectra:

$^1$H NMR (300 MHz, CDCl$_3$/TMS): δ 7.57 (d, 2H, J=7.8 Hz), 7.40-7.23 (m, 5H), 7.18-7.00 (m, 8H), 6.72 (s, 1H), 5.42-5.30 (m, 6H), 3.81 (m, 1H), 2.90-2.70 (m, 4H), 2.47-2.20 (m, 2H), 2.13-1.90 (m, 4H), 1.40-1.25 (m, 10H), 0.97 (t, 3H, J=7.5 Hz).

Example 12

ALA-Hydroxy Methyl Ester

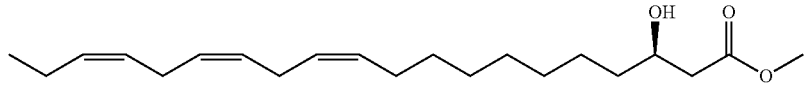 [SMILES: CC/C=C\C/C=C\C/C=C\CCCCCCC[C@@H](O)CC(=O)OC]

The ALA-Hytra condensation product (prepared in Example 11, 5.50 g, 9.24 mmol) was dissolved in anhydrous methanol (200 mL) under an argon atmosphere, cooled in a water/ice bath, and 0.5 M sodium methoxide solution in methanol (40 mL) was added. The solution stirred for 4 hours with continued cooling under argon. After 2 hours, 5% hydrochloric acid solution (100 mL) was added and the methanol was removed on a rotary evaporator. The residue was stirred in 100 mL of water, and extracted with dichloromethane (100 mL). The aqueous layer was extracted a second time with dichloromethane (50 mL). The dichloromethane extracts were combined, dried over magnesium sulfate, filtered and concentrated. The remaining oil was mixed with heptane (50 mL) and stored in a freezer overnight. The solid ((S)-1,1,2-triphenylethane-1,2-diol) was removed by filtration, washing with cold heptane (10 mL). The heptane filtrate was concentrated and purified over silica gel (80 g) eluting with 20% ethyl acetate in heptane. The experiment produced the ALA-hydroxy methyl ester as a clear oil (2.27 g, 67% yield) that still contained a trace of (S)-1,1,2-triphenylethane-1,2-diol (10-20%) and is characterized by the following spectra:

$^1$H NMR (300 MHz, CDCl$_3$/TMS): δ 5.42-5.30 (m, 6H), 4.0 (m, 1H), 3.71 (s, 3H), 2.85-2.70 (m, 4H), 2.55-2.36 (m, 2H), 2.10-1.98 (m, 4H), 1.54-1.25 (m, 12H), 0.98 (t, 3H, J=7.5 Hz).

Example 13

ALA-Keto Ester

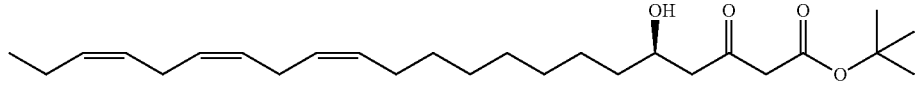 [SMILES: CC/C=C\C/C=C\C/C=C\CCCCCCC[C@@H](O)CC(=O)CC(=O)OC(C)(C)C]

t-Butyl acetate (4.0 g, 34 mmol) was dissolved in THF (40 mL) under an argon atmosphere. The solution was cooled in an acetone/dry ice bath to −78° C. Lithium diisopropylamide solution (2.0 M, 14 mL, 28 mmol) was added drop-wise over 5 minutes. The solution was allowed to stir for 30 minutes at −78° C. The ALA-hydroxy methyl ester (2.27 g, 6.7 mmol) in THF (5 mL) was added drop-wise over 5 minutes at −78° C. The mixture was slowly warmed to −50° C. over 1 hour. The temperature of the reaction mixture was maintained at −50° C. for 2 hours and then was slowly warmed to −15° C. over 2 hours. The solution was stirred at −15° C. for 20 minutes, and was quenched with addition of saturated ammonium chloride solution (5 mL). The solution was diluted with 5% hydrochloric acid solution (100 mL) and extracted with ethyl acetate (2×50 mL). The ethyl acetate extracts were combined, dried over sodium sulfate, filtered, and concentrated. The crude material (5.4 g) was purified by column chromatography on silica gel (80 g) eluting with 20% ethyl acetate in heptane. The experiment produced the ALA-keto ester (2.79 g, 98% yield) as a light yellow oil. The material contained some of the ester starting material (5%) along with the ((S)-1,1,2-triphenylethane-1,2-diol) (10%) from the previous step and t-butyl acetate. The product was used without additional purification for the next step and the crude product was characterized by the following spectra:

$^1$H NMR (300 MHz, CDCl$_3$/TMS): δ 5.42-5.30 (m, 6H), 4.06 (m, 1H), 3.38 (s, 2H), 2.85-2.75 (m, 4H), 2.75-2.52 (m, 2H), 2.10-1.98 (m, 4H), 1.54-1.25 (m, 12H), 1.47 (s, 9H), 0.98 (t, 3H, J=7.5 Hz).

Example 14

ALA-Dihydroxy t-Butyl Ester

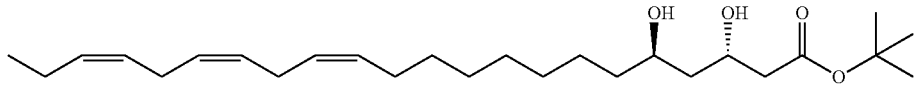 [SMILES: CC/C=C\C/C=C\C/C=C\CCCCCCC[C@@H](O)C[C@H](O)CC(=O)OC(C)(C)C]

The ALA-keto-ester (prepared in Example 13, 2.70 g, 6.42 mmol) was dissolved in THF (40 mL) and methanol (10 mL) under argon. The flask was cooled to 5° C. and 1M diethylmethoxy borane solution (7 mL) was added drop-wise over 5 minutes. After 20 minutes, the solution was cooled to −78° C. in a dry ice/acetone bath. Sodium borohydride (600 mg, 15.8 mmol) was added and the mixture stirred for 3 hours at −78° C. The mixture was slowly warmed to −25° C. over 45 minutes. At −25° C., a solution of THF (30 mL) and water (10 mL) containing sodium acetate (1.0 g) was added. Hydrogen peroxide solution (30%, 10 mL) was added drop-wise over 5-10 minutes and the solution was allowed to warm to RT over 2 hours. The solution stirred for an additional 30 minutes at RT. The solution was cooled again in an ice/water bath and saturated sodium sulfite solution (25 mL) was added drop-wise over 30 minutes. The reaction mixture was extracted with ethyl acetate (2×25 mL). The combined ethyl acetate extracts were washed with water (2×25 mL), dried over sodium sulfate, filtered, and concentrated. The crude oil (2.70 g) was purified by column chromatography on silica gel (80 g), eluting with 20% ethyl acetate in heptane. The experiment produced the ALA-dihydroxy t-butyl ester (2.09 g, 77% yield) as a clear oil, which still contained some of the undesired isomer (25%) and is characterized by the following spectra:

$^1$H NMR (300 MHz, CDCl$_3$/TMS): δ 5.42-5.25 (m, 6H), 4.22 (m, 1H), 3.71 (m, 1H), 2.85-2.75 (m, 4H), 2.57-2.25 (m, 2H), 2.10-1.90 (m, 4H), 1.60-1.25 (m, 14H), 1.47 (s, 9H), 0.98 (t, 3H, J=7.5 Hz).

Example 15

ALA-Lactone

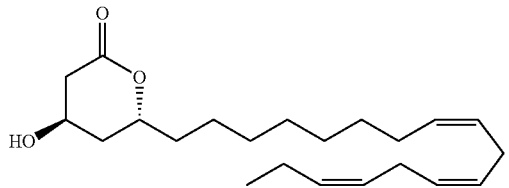 [SMILES: CC/C=C\C/C=C\C/C=C\CCCCCCC[C@@H]1C[C@@H](O)CC(=O)O1]

The ALA-dihydroxy t-butyl ester (2.0 g, 4.7 mmol) was dissolved in dichloromethane (40 mL) under an argon atmosphere. Trifluoroacetic acid (4 mL) was added and the solution stirred for 24 hours under argon at RT. The solution was concentrated and the crude lactone was purified by column chromatography on silica gel (50 g), eluting with 40% ethyl acetate in heptane. The experiment generated the ALA-lactone (0.68 g, 41% yield) as a clear oil and is characterized by the following characteristics and spectra:

| | |
|---|---|
| Name: | (4R,6R)-6-((8Z,11Z,14Z)-heptadeca-8,11,14-trienyl)-4-hydroxytetrahydro-2H-pyran-2-one |
| Appearance: | colorless oil |
| Chemical Formula: | C$_{22}$H$_{36}$O$_3$ |
| Molecular Weight: | 348.52 |
| Chromatographic purity (HPLC): | 94.2% (rt = 6.507 min, 90-100% MeOH in H$_2$O over 15 minutes, Altima C18, 5μ, 4.6 × 250 mm, 1.0 mL/min, 10 μL injection, 40° C., UV detection, 210 nm). |
| HRMS (MMI-TOF-MS): | Calculated for C$_{22}$H$_{37}$O$_3$ (M + H)$^+$: 349.2737; found: 349.2732. |
| Optical Rotation: | [α]$_D^{22}$ = +8.626 (c = 1.56, ethanol) |
| $^1$H NMR (300 MHz, CDCl$_3$/TMS): | δ 5.45-5.25 (m, 6 H), 4.68 (m, 1H), 4.40 (m, 1H), 2.88-2.72 (m, 4H), 2.13-1.90 (m, 6H), 1.80-1.25 (m, 14H), 0.98 (t, 3H, J = 7.8 Hz). |

Example 16

ALA-Lactone, Sodium Salt

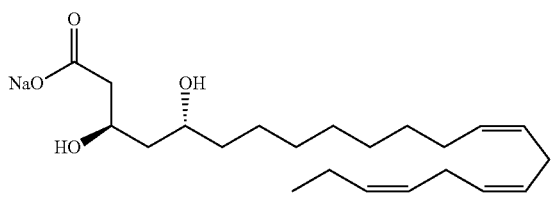

The ALA-lactone (prepared in Example 15, 110 mg, 0.32 mmol) was dissolved in THF (2 mL) and methanol (2 mL) under an argon atmosphere. To the solution was added sodium hydroxide (13 mg, 0.33 mmol) in water (2 mL). The solution stirred for 5 hours at RT under argon. The solution was concentrated and dried under high vacuum. The experiment produced the sodium salt of ALA-lactone as a clear glass (120 mg, 98% yield, 96.9% purity by HPLC) and is characterized by the following spectra:

$^1$H NMR (300 MHz, CD$_3$OD/TMS): δ 5.45-5.25 (m, 6H), 4.09 (m, 1H), 3.75 (m, 1H), 2.88-2.72 (m, 4H), 2.40-2.22 (m, 2H), 2.13-2.03 (m, 4H), 1.59 (t, 2H, J=6.6 Hz), 1.50-1.25 (m, 14H), 0.97 (t, 3H, J=7.8 Hz).

Utility:

The utility of the compounds of Formula (I) and Formula (II) are provided below using the following materials and techniques as referenced in the procedure below:

1. SigmaAldrich. HMG-CoA Reductase Assay Kit sufficient for 30 assays (1 mL), sufficient for 100 assays (200 μL). In: catalog number CS 1090. http://www.signaaldrich-.com/catalog/product/sigma/cs1090?lang=en&region=HR. April, 2015.
2. Holdgate G, Ward W, McTaggart F. Molecular mechanism for inhibition of 3-hydroxy-3-methylglutaryl CoA (HMG-CoA) reductase by rosuvastatin. Biochemical Society Transactions. 2003; 31(3):528-31.
3. Louis-Flamberg P, Peishoff C E, Bryan D L, Leber J, Elliott J D, Metcalf B W et al. Slow binding inhibition of 3-hydroxy-3-methylglutaryl-coenzyme A reductase. Biochemistry. 1990; 29(17):4115-20.
4. Nakamura C E, Abeles R H. Mode of interaction of .beta.-hydroxy-.beta.-methylglutaryl coenzyme A reductase with strong binding inhibitors: compactin and related compounds. Biochemistry. 1985; 24(6):1364-76.
5. Istvan E S, Palnitkar M, Buchanan S K, Deisenhofer J. Crystal structure of the catalytic portion of human HMG-CoA reductase: insights into regulation of activity and catalysis. The EMBO journal. 2000; 19(5):819-30.
6. Motulsky H, Christopoulos A. Fitting Models to Biological Data Using Linear and Nonlinear Regression: A Practical Guide to Curve Fitting Oxford University Press, USA; 1 edition 2004.

Procedure:

The HMG-Co-A reductase inhibition activity, dose-response curves for Na+ salts of EPA-statin, ALA-statin, and reference pravastatin were measured using standard assay kits from Sigma-Aldrich [1]. The kit was assembled following the earlier studies of HMG reductase activity and inhibition [2-4]. Briefly, the dose-response curves have been measured using soluble catalytic domain fragment of human HMG reductase [5]. Human HMG reductase (3-hydroxy-3-methylglutaryl-CoA reductase) is a multidomain transmembrane protein composed of insoluble transmembrane segment and soluble catalytic domain [5]. The activity was measured by following decrease in a sample's absorbance at 340 nm caused by enzymatic oxidation of NADP(H) in presence of coenzyme A. Assay mix was prepared using sub-saturating concentrations of NADP(H) and coenzyme CoA, to avoid distortion of dose-response curves that can be caused by competition with the substrate [6]. NADP(H) concentration in the assay mix was adjusted to 250 μM. The enzyme concentration in assays mix were adjusted to measure initial velocity steady state rates in the range between 20 to 24 μM of NADP(H) per one minutes [6]. Stock solutions of Na salts of EPA-statin, ALA-statin were prepared in assay buffer in concentration of 50 mM, and subsequently diluted to lower concentrations in the same buffer as needed.

The relative activity is presented in the FIG. 1. A summary of these results are presented in Table 1 below.

TABLE 1

| Inhibitor | IC50 μM error | activity without inhibitor μM*min−1 | Hill coefficient |
|---|---|---|---|
| EPA-statin, Na salt | 94 ± 8 | 20.2 ± 0.9 | 1.6 ± 0.6 |
| ALA-statin, Na salt | 25 ± 7 | 23.9 ± 0.8 | 1.3 ± 0.3 |
| Pravastatin* | 1.2 ± 1 | 20.4 ± 0.9 | 1.4 ± 0.4 |

*based on information from Sigma-Aldrich which stated that the concentration of provided pravastatin stock solution was 1 μg/μL.

The summary results indicate that EPA-statin is about $1/100^{th}$ the potency of pravastatin, and ALA-statin about $1/20^{th}$ as potent in inhibiting HMG-CO-A-reductase enzyme.

Although the invention has been described with reference to its preferred embodiments, those of ordinary skill in the art may, upon reading and understanding this disclosure, appreciate changes and modifications which may be made which do not depart from the scope and spirit of the invention as described above or claimed hereafter.

What is claimed is:

1. A compound of Formula (I) or Formula (II) having the formula:

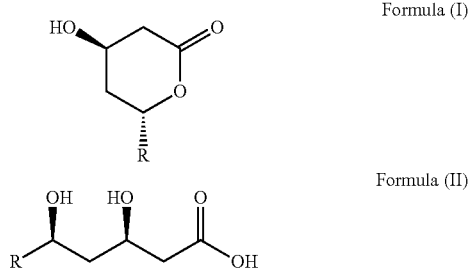

wherein:
R is joined from the aldehyde group formed by the partial reduction of the carboxylic acid of:
cis,cis,cis-7,10,13-hexadecatrienoic acid (HTA) of the following structure:

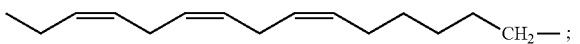

cis,cis,cis-9,12,15-octadecatrienoic acid (ALA) of the following structure:

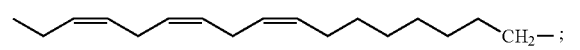

cis,cis,cis,cis-6,9,12,15-octadecatetraenoic acid (SDA) of the following structure:

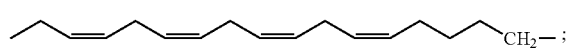

cis,cis,cis-11,14,17-eicosatrienoic acid (ETE) of the following structure:

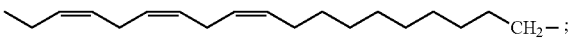

cis,cis,cis,cis-8,11,14,17-eicosatetraenoic acid (ETA), of the following structure:

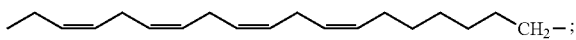

cis,cis,cis,cis-5,8,11,4,17-eicosapentanenoic acid (EPA) of the following structure:

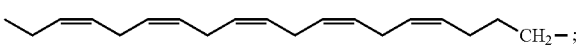

cis,cis,cis,cis,cis-6,9,12,15,18-heneicosapentaenoic acid (HPA) of the following structure:

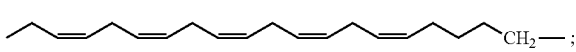

cis,cis,cis,cis,cis-7,10,13,16,19-docosapentaenoic acid (DPA) of the following structure:

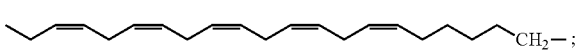

cis,cis,cis,cis,cis-4,7,10,13,16,19-docosahexaenoic acid (DHA) of the following structure:

cis,cis,cis,cis-9,12,15,18,21-tetracosapentaeonic acid (TPA) of the following structure:

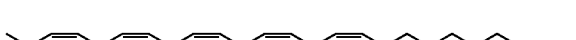

or
cis,cis,cis,cis,cis-6,9,12,15,18,21-tetracosahexaeonic acid (THA) of the following structure:

or
the pharmaceutically-acceptable salts of Formula (II).

2. The compound of claim 1 wherein the compound of Formula (I) or (II) is ≥95% chemical purity.

3. A pharmaceutical formulation having as its active ingredient one or more compounds of Formula (I) or Formula (II) and its pharmaceutically-acceptable salts, as defined in claim 1, with pharmaceutically-acceptable adjuvants, binders, desiccants, diluents and excipients.

4. The pharmaceutical formulation of claim 3 having as its active ingredient a compound of Formula (II) or its pharmaceutically-acceptable salts in the form of soft or hard gelatin capsule or tablet, or a solution for injection, ampule, emulsion, or suspension.

5. The pharmaceutical formulation of claim 3 having as its active ingredient a compound of Formula (I) in the form of a soft or hard gelatin capsule, or tablet.

6. The pharmaceutical formulation of claim 4 wherein the effective amount of the formulation is from about 10 mg to about 500 mg/day.

7. The pharmaceutical formulation of claim 5 wherein the effective amount of the formulation is from about 10 mg to about 5.00 mg/day.

* * * * *